US00PP36973P2

(12) United States Plant Patent
Meilland

(10) Patent No.: US PP36,973 P2
(45) Date of Patent: Sep. 23, 2025

(54) BEDDING ROSE PLANT NAMED 'MEISOBUKO'

(50) Latin Name: *Rosa hybrida*
Varietal Denomination: MEISOBUKO

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/978,140

(22) Filed: Dec. 12, 2024

(51) Int. Cl.
*A01H 5/02* (2018.01)
*A01H 6/74* (2018.01)

(52) U.S. Cl.
USPC ..... Plt./101

(58) Field of Classification Search
USPC ..... Plt./101, 146, 105
CPC . A01H 5/02; A01H 5/00; A01H 6/749; A01H 6/74
See application file for complete search history.

(56) References Cited

U.S. PATENT DOCUMENTS

PP9,652 P * 10/1996 Meilland ..... Plt./122
PP23,122 P2 10/2012 Kordes

OTHER PUBLICATIONS

Issuu 2025 Bloomables Brand Brochure, retrieved on Mar. 5, 2025 at https://issuu.com/starrosesandplants/docs/2025bloomablesbrochure, cover page, pp. 1,2,8-9, 5 pp. total. (Year: 2025).*

Issuu Star Roses and Plants Rose Catalog 2025 retrieved on Mar. 5, 2025 at https://issuu.com/starrosesandplants/docs/2025_rosecatalog, cover page, pp. 1, 8, 71, 4 pp. total. (Year: 2025).*

Help Me Find Roses, Clematis and Peonies and everything gardening related, Conard-Pyle (Star Roses); https://helpmefind.com/gardening/l.php?l=18.3057 (downloaded on Jan. 27, 2025) one page.

Star Roses and Plants—Our History, https://starrosesandplants.com/industry/about-us/history/ (downloaded on Jan. 27, 2025) 18 pp.

* cited by examiner

*Primary Examiner* — June Hwu

(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEISOBUKO', is described. The new variety forms in abundance on a nearly continuous basis geranium red-orange colored blossoms. The growth habit is bushy. Glossy and dense foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'MEISOBUKO'.

STATEMENT REGARDING PRIOR DISCLOSURES BY THE INVENTOR

The first sale or offer for sale of the new variety was Jan. 22, 2024, in the United States of America from STAR® Roses and Plants. The first offer for sale of the new variety, and subsequent offer for sales and sales, was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding in Le Cannet des Maures, Var, France by artificial pollination wherein two parents were crossed which previously had been studied in the hope that they would contribute the desired characteristics. The female parent (i.e., the seed parent) of the new variety was the 'KORschwill' variety (U.S. Plant Pat. No. 23,122). The male parent (i.e., the pollen parent) of the new variety was an unnamed seedling (not patented) which is the product of the cross between the 'NOACAS' variety (not patented) and an unnamed breeder seedling (not patented).

The parentage of the new variety can be summarized as follows:

'KORschwill' x ('NOACAS' x unnamed breeder seedling)

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms geranium red-orange colored blossoms, (b) exhibits a bushy growth habit, and (c) provides a glossy foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the 'KORschwill' variety (i.e., the seed parent) provides a shrub growth habit which exhibits a taller growth habit compared to the more compact, bushy growth habit of the bedding rose new variety. Additionally, the new variety displays geranium red-orange colored flowers, whereas the unnamed seedling male parent (i.e., the pollen parent) displays purple-red and white bicolor flowers. Moreover, the new variety can be readily distinguished from non-parental related similar varieties. For example, the 'MEIFERJAC' variety (U.S. Plant Pat. No. 9,652) has a shorter plant height compared to the new variety and has lower stamen number of approximately 77, whereas the new variety has stamen number typically between 90-110.

The new variety has been named the 'MEISOBUKO' variety.

BRIEF DESCRIPTION OF THE PHOTOGRAPHS

The accompanying photograph shows, as nearly true as it is reasonably possible to make the same in a color illustration of this character, typical specimens of the plant parts of the new variety. The rose plants of the new variety were approximately one year of age and were observed during July while budded on *Rosa laxa* and growing outdoors at Le Cannet des Maures, Var, France. Dimensions in centimeters are indicated at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designation used herein represents the closest color observed on the majority of the specified botanical feature. The description is based on a one-year-old specimen of the new variety, observed during July, while budded on *Rosa laxa* and growing outdoors at Le Cannet des Maures, Var, France.

Botanical classification: *Rosa hybrida* cultivar 'MEISOBUKO'.

Commercial classification: Bedding Rose Plant.

Plant:

*Habit*.—Bushy, well suited as a container plant.

*Height*.—Approximately 60.0 cm on average.

*Width*.—Approximately 60.0 cm on average.

Branches:

*Stem color*.—Young stems: Yellow-Green Group 144B. adult wood: Yellow-Green Group 144A more or less suffused with Yellow-Green Group 146B.

*Length*.—From the crown to the flower is approximately 33.0 cm on average.

*Diameter*.—Approximately 0.6 cm on average.

*Prickles*.—Configuration on adult stems: upright, elongated and curved downwards on the upper surface and very concave on the under surface. — long prickles — quantity: approximately 5 thorns on average per 10 cm long young stem and approximately 10 thorns on average per 10 cm long adult stem. — long prickles — length: approximately 0.5 cm on average on young stems and approximately 0.7 cm on average on adult stems. — long prickles — length at base: approximately 0.7 cm on average on young stems and approximately 0.6 cm on average on adult stems. — long prickles — width at base: approximately 0.2 cm on average on young stems and typically between 0.2 cm and 0.3 cm on adult stems. — long prickles — base shape: elliptical, very narrow, and long on young stems; obovate, broad, and short on adult stems. — long prickles — color on young stems: Yellow-Green Group 144B. — long prickles — color on adult stems: Greyed-Orange Group 165B more or less suffused with Greyed-Orange Group 165A. — small prickles of less than 0.5 cm — quantity: none observed.

*Anthocyanin coloration of young shoots*.—Greyed-Purple Group 183A.

*Internode numbers on entire branch*.—Typically between 6 to 9.

*Internode length*.—Typically between 3.0 cm to 7.0 cm.

Leaflets:

*Number*.—3, 7, and most often 5.

*Shape*.—Tip: acuminate. base: obtuse.

*Serration*.—Small and single.

*General appearance*.—Elliptical.

*Undulation*.—Weak.

*Glossiness of upper side*.—Medium.

*Texture*.—Moderately leathery.

*Smoothness*.—Upper surface: smooth. — under surface: bumpy.

*Venation*.—Color is Yellow-Green Group 144B (barely visible); and pattern is imparipinnate.

*Size*.—Terminal leaflet: length is typically between 4.5 cm to 6.0 cm; width is typically between 3.0 cm to 3.5 cm. — 5-leaflet leaf: length is approximately 12.0 cm on average; width is approximately 10.0 cm on average.

Foliage:

*General appearance*.—Very dense with a glossy aspect.

*New foliage*.—Upper surface color: a color between Green Group 137A and Yellow-Green Group 146A. — under surface color: Green Group 137C.

*Adult foliage*.—Upper surface color: a color between Green Group 139A and Yellow-Green Group 147A. — under surface color: Green Group 137C.

*Petiole*.—Texture: upper surface is smooth; under surface is smooth. — length: approximately 4.1 cm on average. — width: approximately 0.1 cm on average. — upper surface color: Yellow-Green Group 144B in the center and Green Group 143A along the edges. — under surface color: Yellow-Green Group 144B.

*Rachis*.—Rachis length of terminal leaflet: approximately 2.7 cm on average. — rachis width of terminal leaflet: approximately 0.1 cm on average. — texture: upper surface is smooth; under surface is smooth. — upper surface color: Yellow-Green Group 144B in the center and Green Group 137A along the edges. — under surface color: Yellow-Green Group 144B.

*Stipules*.—Length: typically between 1.5 to 2.5 cm. — width: typically between 0.2 to 0.3 cm. — general appearance: narrow. — texture: upper surface is smooth; under surface is smooth. — upper surface color: Green Group 137A with a small zone along the petiole of Yellow-Green Group 144B. — under surface color: Green Group 137C with a small zone along the petiole of Yellow-Green Group 144B.

Inflorescence:

*Number of flowers per stem*.—Typically between 3 to 7 flowers per stem.

*Lastingness of the bloom*.—On the plant: approximately 15 days on average. — in vase: not tested.

*Bud*.—Shape: ovoid. — size: small. — length: approximately 2.0 cm on average. — width: approximately 1.3 cm on average. — color as calyx breaks: upper surface: a color between Red Group 44B and Red Group 40A; basal spot is White Group 155B. under surface: White group 155B more or less suffused with Red Group 47C; basal spot is White Group 155B.

*Sepals*.—Number: commonly 5. — length: approximately 2.0 cm on average. — width: approximately 0.5 cm on average. — shape: at the top: elongated and narrow. at the base: flat at union with the receptacle. — extensions: typically 4 sepals with no extensions and 1 sepal with weak extension. — upper surface: texture: tomentous. color: Yellow-Green Group 144B, completely covered with many hairs of White Group 155A. — under surface: texture: smooth. color: Yellow-Green Group 144B more or less suffused with Yellow-Green Group 144A.

*Receptacle*.—Color: Yellow-Green Group 144B. — length: approximately 0.7 cm on average. — width: approximately 0.5 cm on average. — surface: smooth. — shape: pitcher shaped.

*Peduncle*.—Length: typically between 1.8 cm to 6.0 cm on average. — width: approximately 0.2 cm on average. — surface: smooth. — color: Yellow-Green Group 144B.

*Flower*.—Diameter when open: approximately 4.5 cm on average. — depth of the flower: typically between 2.0 to 2.5 cm on average. — shape: flat cup shaped. — shape when viewed from above: irregularly rounded. — shape of the upper part of the flower profile: flat. — shape of the lower part of the flower profile: flat. — type: double. — number of petals under normal conditions: approximately 25 on average. — petals: general shape: rounded. shape at the base: acute. shape at the top: slightly acuminate. texture: dry and thick. length: typically between 2.5 cm to 3.0 cm. width: typically between 1.7 cm to 3.0 cm. — undulation of the petal: medium. — reflexing of the petal: strong. — petal incision: very weak. — petal arrangement: imbricated with rare crumpled half petals. — petal drop: petals drop off cleanly before drying. — fragrance: none. — discoloration of the flower: loss of pigment at the end of blooming. — color when opening: basal spot on the upper surface: width is approximately 1.0 cm and height is approximately 0.5 cm on average, White Group 155B. upper surface: Red Group 40A. basal spot on the under surface: White Group 155B. under surface: a color between Red Group 41A and Red Group 41B. — color of the open flower: basal spot on upper surface: width is approximately 1.2 cm and height is approximately 0.6 cm on average, White Group 155B. upper surface: White Group 155B more or less suffused with a color between Red Group 47C and Red Group 47D. basal spot on under surface: White Group 155B. under surface of the flower. White Group 155B more or less suffused with a color between Red Group 47C and Red Group 47D. — anthers: typically between 90 to 110, length is approximately 0.1 cm on average, width is approximately 0.1 cm on average, coloration is Yellow-Orange Group 16B, and arrangement is regular around styles. — filaments: length is typically between 0.3 cm to 0.5 cm, and coloration is Red-Purple Group 57B. — styles: length is approximately 1.3 cm on average, coloration is Yellow Group 8D, and number is typically between 50 to 55. — stigmas: length is typically less than 0.1 cm and coloration is Yellow Group 8D. — pollen: abundant quantity; color is Yellow-Orange Group 22A. — hips: rarely present.

Development:

*Vegetation*.—Very strong.

*Blossoming*.—Early in the season, very abundant and nearly continuous (typically from May to first frost in France).

*Resistance to diseases*.—Very good resistance for rust (*Phragmidium* sp.) and powdery mildew (*Podosphaera pannosa*).

*Hardiness*.—Tested up to USDA Zone 5.

The new 'MEISOBUKO' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of bedding rose plant named 'MEISOBUKO' characterized by the following combination of characteristics:

(a) forms geranium red-orange colored blossoms, (b) exhibits a bushy growth habit, and (c) provides a glossy foliage;

substantially as herein shown and described.

* * * * *

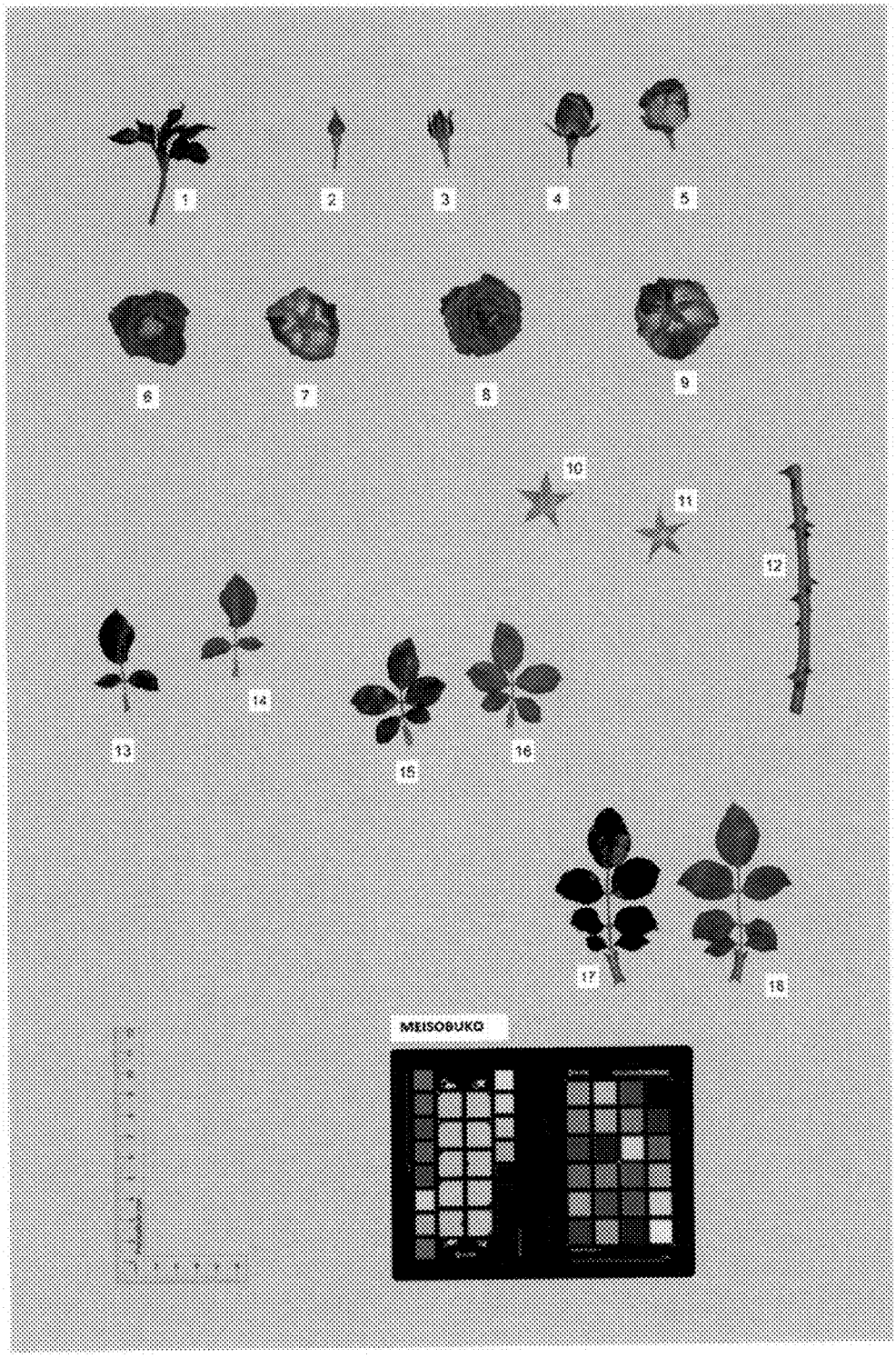
1
2
3
4
5
6
7
8
9
10
11
12
13
14
15
16
17
18
MEISOBUKO